(12) United States Patent
Nonogaki

(10) Patent No.: US 7,658,769 B2
(45) Date of Patent: Feb. 9, 2010

(54) OXIDATION HAIR DYE COMPOSITION

(75) Inventor: Tsuyoshi Nonogaki, Aichi-ken (JP)

(73) Assignee: Hoyu Co., Ltd., Aichi-ken (JP)

( * ) Notice: Subject to any disclaimer, the term of this patent is extended or adjusted under 35 U.S.C. 154(b) by 81 days.

(21) Appl. No.: 11/914,687

(22) PCT Filed: Nov. 6, 2006

(86) PCT No.: PCT/JP2006/322100

§ 371 (c)(1),
(2), (4) Date: Nov. 16, 2007

(87) PCT Pub. No.: WO2007/055173

PCT Pub. Date: May 18, 2007

(65) Prior Publication Data

US 2009/0089940 A1    Apr. 9, 2009

(30) Foreign Application Priority Data

Nov. 11, 2005  (JP)  ............................ P2005-328017
Oct. 11, 2006  (JP)  ............................ P2006-277523

(51) Int. Cl.
*A61Q 5/10* (2006.01)

(52) U.S. Cl. ........................ 8/405; 8/406; 8/587; 8/588; 8/594

(58) Field of Classification Search .................... 8/405, 8/406, 435, 587, 588, 594

See application file for complete search history.

(56) References Cited

U.S. PATENT DOCUMENTS 6,497,889 B2 * 12/2002 Takekoshi et al. ........... 424/401
2005/0124798 A1  6/2005 Quinn et al.

FOREIGN PATENT DOCUMENTS

| JP | 64-56611 A | | 3/1989 |
| JP | 94-056611 | * | 3/1989 |
| JP | 4-97000 A | | 3/1992 |
| JP | 5-43437 A | | 2/1993 |
| JP | 8-268848 A | | 10/1996 |
| JP | 10-87450 A | | 4/1998 |
| JP | 11-180836 A | | 7/1999 |
| JP | 2001-97834 A | | 4/2001 |
| JP | 2005-60234 A | | 3/2005 |
| WO | 01/45656 A1 | | 6/2001 |
| WO | 03/054025 A2 | | 7/2003 |

* cited by examiner

*Primary Examiner*—Eisa B Elhilo
(74) *Attorney, Agent, or Firm*—Crompton, Seager & Tufte, LLC

(57) ABSTRACT

An oxidation hair dye composition that provides an improved dyeing property. The oxidation hair dye composition comprises an oxidation dye, an alkaline chemical, and an oxidizing agent. The oxidation hair dye composition further comprises at least one selected from the group consisting of microbial hyaluronic acids and salts thereof.

5 Claims, No Drawings

OXIDATION HAIR DYE COMPOSITION

FIELD OF THE INVENTION

The present invention relates to an oxidation hair dye composition that provides an improved dyeing property.

BACKGROUND OF THE INVENTION

An oxidation hair dye composition comprising an oxidation dye and an oxidizing agent for color developing the oxidation dye is generally known. This oxidation hair dye composition of a liquid formulation thereof for improving the permeability typically also contains an alkaline chemical to elevate the pH of the oxidation dye. However, it has generally not been easy to improve the hair-dyeing property of the oxidation hair dye composition by only containment of the alkaline chemical because the elevated pH of the liquid formulation poses a problem in that it makes the hair susceptible to damage. An oxidation hair dye composition as described in patent document 1 has been previously known. This oxidation hair dye composition comprises a mucopolysaccharide to improve the dyeing property thereof. Examples of the mucopolysaccharide include animal-derived hyaluronic acids and mucoitinsulfuric acid.

Patent document 1: Japanese Laid-Open Patent Publication No. 64-56611

SUMMARY OF THE INVENTION

However, the mucopolysaccharide has had a problem in that it cannot sufficiently improve the dyeing property. In addition, there has been a problem in that when the content of the mucopolysaccharide is simply increased in order to improve the dyeing property to a certain extent, the viscosity of the liquid formulation is elevated.

Accordingly, as a result of intensive studies, the present inventors have found that among other mucopolysaccharides, a microbial hyaluronic acid is compounded to solve the above-described problems, thereby achieving the invention. An object of the invention is to provide an oxidation hair dye composition that provides an improved dyeing property.

One aspect of the invention provides an oxidation hair dye composition comprising an oxidation dye, an alkaline chemical, and an oxidizing agent. This oxidation hair dye composition further comprises at least one selected from the group consisting of microbial hyaluronic acids and salts thereof. The content of at least one selected from the group consisting of the microbial hyaluronic acids and salts thereof in the oxidation hair dye composition is preferably 0.00001 to 0.3 mass %.

The oxidation hair dye composition further comprises at least one selected preferably from the group consisting of hydroxymethoxybenzophenonesulfonic acid, dihydroxydimethoxybenzophenonedisulfonic acid, pantetheine-S-sulfonic acid, aminoethylsulfonic acid, guaiazulenesulfonic acid, para-phenolsulfonic acid, and salts thereof.

The ratio of the content of the above-described at least one selected from the group consisting of microbial hyaluronic acids and salts thereof to the content of the above-described at least one selected from the group consisting of hydroxymethoxybenzophenonesulfonic acid, dihydroxydimethoxybenzophenonedisulfonic acid, pantetheine-S-sulfonic acid, aminoethylsulfonic acid, guaiazulenesulfonic acid, para-phenolsulfonic acid, and salts thereof is preferably 1:100 to 100:1.

The content of at least one selected from the group consisting of the hydroxymethoxybenzophenonesulfonic acid, dihydroxydimethoxybenzophenonedisulfonic acid, pantetheine-S-sulfonic acid, aminoethylsulfonic acid, guaiazulenesulfonic acid, para-phenolsulfonic acid, and salts thereof in the oxidation hair dye composition is preferably 0.000001 to 5 mass %.

DETAILED DESCRIPTION OF THE PREFERRED EMBODIMENTS

The present invention is described below in detail, referring to an embodiment implemented for an oxidation hair dye composition.

The oxidation hair dye composition of the present embodiment is composed, for example, of a first agent and a second agent. The first agent comprises an oxidation dye, an alkaline chemical, and at least one selected from the group consisting of microbial hyaluronic acids and salts thereof. To further improve the hair-dyeing property, it is preferred that the first agent additionally comprises at least one selected from the group consisting of hydroxymethoxybenzophenonesulfonic acid, dihydroxydimethoxybenzophenonedisulfonic acid, pantetheine-S-sulfonic acid, aminoethylsulfonic acid (taurine), guaiazulenesulfonic acid, para-phenolsulfonic acid, and salts thereof. In the following description, at least one selected from the group consisting of microbial hyaluronic acids and salts thereof is called hyaluronic acids. In addition, at least one selected from the group consisting of hydroxymethoxybenzophenonesulfonic acid, dihydroxydimethoxybenzophenonedisulfonic acid, pantetheine-S-sulfonic acid, aminoethylsulfonic acid (taurine), guaiazulenesulfonic acid, para-phenolsulfonic acid, and salts thereof is called sulfonic acids. The second agent comprises an oxidizing agent. In dyeing the hair, the first and second agents are mixed to provide the oxidation hair dye composition. This oxidation hair dye composition is applied to the hair to dye the hair.

First Agent

The first agent according to the present embodiment comprises the oxidation dye, the alkaline chemical, and hyaluronic acids. The first agent preferably comprises sulfonic acids. This first agent may further comprise components generally used in a first agent in an oxidation hair dye, as other components.

The oxidation dye is a compound capable of being color developed by oxidation polymerization using an oxidizing agent to be described, and specifically divided into a major intermediate and a coupler. Examples of the major intermediate include phenylenediamines or salts thereof, aminophenols or salts thereof, and diaminopyridines or salts thereof. Examples of such salts include hydrochlorides, sulfates, and acetates. These major intermediates may be contained alone or in a combination of two kinds or more. Examples of the major intermediate include p-phenylenediamine, toluene-2,5-diamine, N,N-bis(2-hydroxyethyl)-p-phenylenediamine, N-(2-hydroxyethyl)-N-ethyl-p-phenylenediamine, 2-(2-hydroxyethyl)-p-phenylenediamine, p-aminophenol, and salts thereof.

Examples of the coupler include resorcin, pyrogallol, catechol, m-aminophenol, m-phenylenediamine, o-aminophenol, 2,4-diaminophenol, 1,2,4-benzenetriol, toluene-3,4-diamine, toluene-2,4-diamine, hydroquinone, α-naphthol, 2,6-diaminopyridine, 1,5-dihydroxynaphthalene, 5-amino-o-cresol, diphenylamine, p-methylaminophenol, phloroglucin, 2,4-diaminophenoxyethanol, gallic acid, tannic acid, ethyl gallate, methyl gallate, propyl gallate, nutgall, 1-methoxy-2- amino-4-(2-hydroxyethyl)aminobenzene, 5-(2-hydroxyethylamino)-2-methylphenol, and salts thereof. These couplers may be contained alone or in a combination of two kinds or more.

In order that the oxidation dye may be capable of dying hair into a color with a diverse color tone, the oxidation dye is preferably composed of at least one selected from major intermediates and at least one selected from couplers.

The content of the oxidation dye in the oxidation hair dye composition is preferably 0.02 to 30 mass %, more preferably 0.2 to 20 mass %. An oxidation dye content of less than 0.02 mass % may not provide a sufficient dyeing property. On the other hand, an oxidation dye content of more than 30 mass % is not economical because it does not provide a further improved dyeing property commensurate therewith.

The content of the main intermediate in the oxidation hair dye composition is preferably 0.01 to 15 mass %, more preferably 0.1 to 10 mass %. A main intermediate content of less than 0.01 mass % may not provide a sufficient dyeing property. On the other hand, a main intermediate content of more than 15 mass % is not economical because it does not provide a further improved dyeing property commensurate therewith. The main intermediate content of 0.1 mass % or more provides an excellent hair-dyeing property. However, the main intermediate content of more than 10 mass % makes it less easy to further improve the dyeing property.

The content of the coupler in the oxidation hair dye composition is preferably 0.01 to 15 mass %, more preferably 0.1 to 10 mass %. A coupler content of less than 0.01 mass % may not provide a sufficient dyeing property. On the other hand, a coupler content of more than 15 mass % is not economical because it does not provide a further improved dyeing property commensurate therewith. The coupler content of 0.1 mass % or more provides a more excellent dyeing property. However, the coupler content of more than 10 mass % makes it more difficult to further improve the dyeing property.

In addition to the above-described oxidation dye, the first agent may contain an oxidation dye as described, for example, in "Iyakubugaihin Genryo Kikaku (Japanese References of Quasi-drug Ingredients)" (issued by Yakuji Nippo Ltd. in June 1991), and a direct dye as a dye other than an oxidation dye.

The alkaline chemical swells the hair to enhance the permeability of an oxidation dye into the hair to improve the dyeing property thereof. Examples of the alkaline chemical include ammonia, alkanolamines, organic amines, inorganic alkalis, basic amino acids, and salts thereof. Examples of the alkanolamines include triethanolamine, diethanolamine, monoethanolamine, isopropanolamine, diisopropanolamine, and 2-amino-2-methyl-1-propanol. Examples of the organic amines include 2-amino-2-methyl-1,3-propanediol and guanidine. Examples of the inorganic alkalis include sodium hydroxide and potassium hydroxide. Examples of the basic amino acids include arginine and lysine. These alkaline chemicals may be contained alone or in a combination of two kinds or more. Two kinds or more of alkaline chemicals may be contained in appropriate combination to impart a buffer action to the first agent. Among these examples of the alkaline chemical, preferred is at least one selected from the group consisting of ammonia and alkanolamines because it makes it easy to improve the permeability of the oxidation dye into the hair.

The content of the alkaline chemical in the oxidation hair dye composition is preferably an amount such that the first agent has a pH of 8 to 12. A pH of the first agent of less than 8 may not sufficiently promote the action of hydrogen peroxide as an oxidizing agent when the first agent is mixed with the second agent. On the other hand, a pH of the first agent of more than 12 is liable to induce troubles such as damage in the hair when the oxidation hair dye composition is applied to the hair.

Hyaluronic acids improve the dyeing property. Examples of salts of hyaluronic acid include alkali metal salts, triethanolamine salts, chitosan salts, and salts with basic amino acids. Examples of the alkali metal salts include sodium salts and potassium salts. Examples of the basic amino acid include lysine and arginine. Hyaluronic acid is a macromolecular polysaccharide having a straight-chain form, and the hyaluronic acid has N-acetylglucosamine and glucuronic acid bound alternately. The molecular weight of the hyaluronic acid is not particularly restricted, but preferably 400,000 to 2,500,000. The kind of the microorganism is not particularly restricted provided that it is a microorganism having the ability to produce hyaluronic acid, but preferably the genus *Streptococcus*, which excretes hyaluronic acid to the outside of the body. Examples of microorganisms of the genus *Streptococcus* include *Streptococcus equi, Streptococcus zooepidemicus, Streptococcus equisimilis, Streptococcus dysgalactiae, Streptococcus pyogenes,* and variants thereof. Examples of a method for extracting the hyaluronic acid from the microorganisms include a method involving fermenting and culturing the microorganisms and then extracting the hyaluronic acid from the culture medium, and a method involving crushing the microorganism cells and thereby extracting the hyaluronic acid from the inside of the body. Among these methods, preferred is the method involving extracting the hyaluronic acid from the fermentation culture medium in view of the ease of extraction and purification. By way of example, when a microorganisms of the genus *Streptococcus* is used, the culture method is preferably a method involving stirring and culturing the microorganisms at 30 to 37° C. under aerobic conditions. A method for purifying the hyaluronic acid may use a known method. By way of example, when the extraction and purification are carried out from a fermentation culture medium, deproteinization is first performed, for example, by use of chloroform. Then, purification using adsorption chromatography such as hydrophobic chromatography and ion exchange chromatography is carried out. The hyalulonic acids properly use commercially available ones. Examples of the commercially available hyalulonic acid include 1% Sodium Biohyaluronate Aqueous Solution (from Shiseido Co., Ltd.), Hyaluronic Acid Solution HA-LQ-1 (from Q.P. Corporation), and Hyaluronic Acid FCH (from Kibun Food Chemifa Co., Ltd.).

The content of the hyaluronic acids in the oxidation hair dye composition is preferably 0.00001 to 0.3 mass %, more preferably 0.0001 to 0.1 mass %. A content of the hyaluronic acids of less than 0.00001 mass % may not sufficiently improve the dyeing property. On the other hand, a content of the hyaluronic acids of more than 0.3 mass % may lead to the increased viscosity of the oxidation hair dye composition. The hyaluronic acids are preferably contained in the first agent in order to prevent the oxidation thereof by the oxidizing agent during the storage of the oxidation hair dye composition.

The sulfonic acids are at least one selected from the group consisting of hydroxymethoxybenzophenonesulfonic acid, dihydroxydimethoxybenzophenonedisulfonic acid, pantetheine-S-sulfonic acid, aminoethylsulfonic acid (taurine), guaiazulenesulfonic acid, and para-phenolsulfonic acid, which have sulfonic acid groups, and salts thereof. Examples of the salt include alkali metal salts, triethanolamine salts, chitosan salts, and salts with basic amino acids. Examples of the alkali metal salts include sodium salts and potassium salts.

Examples of the basic amino acid include arginine and lysine. The sulfonic acids further improve the hair-dyeing property by a synergistic effect with the hyaluronic acids. The sulfonic acids are preferably contained in the first agent in order to prevent the oxidation thereof by the oxidizing agent during the storage of the oxidation hair dye composition.

The content of the sulfonic acids in the oxidation hair dye composition is preferably 0.000001 to 5 mass %, more preferably 0.00001 to 3 mass %. A content of the sulfonic acids of less than 0.000001 mass % may not sufficiently improve the dyeing property. On the other hand, a content of the sulfonic acids of more than 5 mass % may not provide a further improved dyeing property commensurate therewith. In addition, the first agent comprising the sulfonic acids may be discolored with time. To further improve the hair-dyeing property by a synergistic effect between the sulfonic acids and the hyaluronic acids, the ratio of the content of the sulfonic acids to the content of the hyaluronic acids (the content of the sulfonic acids: the content of the hyaluronic acids) is preferably 1:100 to 100:1, more preferably 1:10 to 10:1.

The first agent may contain, as another component, at least one selected, for example, from the group consisting of water, a surfactant, an oily component, and a polyvalent alcohol. Water is contained as a solvent or dispersion medium for each component. The content of water in the oxidation hair dye composition is not particularly restricted.

The surfactant acts as an emulsifying or solubilizing agent to maintain the stability of the first agent. Examples of the surfactant include non-ionic surfactants, cationic surfactants, anionic surfactants, and ampholytic surfactants. Examples of the non-ionic surfactant include ether-type non-ionic surfactants and ester-type non-ionic surfactants. Examples of the ether-type non-ionic surfactant include polyoxyethylene (hereinafter referred to as POE) cetyl ether, POE stearyl ether, POE behenyl ether, POE oleyl ether, POE lauryl ether, POE octyldodecyl ether, POE hexyldecyl ether, POE isostearyl ether, POE nonylphenyl ether, and POE octylphenyl ether.

Examples of the ester-type non-ionic surfactant include POE sorbitan monooleate, POE sorbitan monostearate, POE sorbitan monopalmitate, POE sorbitan monolaurate, POE sorbitan trioleate, POE glycerin monostearate, POE glycerin monomyristate, POE sorbit tetraoleate, POE sorbit hexastearate, POE sorbit monolaurate, POE sorbit beeswax, polyethylene glycol monooleate, polyethylene glycol monostearate, polyethylene glycol monolaurate, lipophilic glycerin monooleate, lipophilic glycerin monostearate, self-emulsifying glycerin monostearate, sorbitan monooleate, sorbitan sesquioleate, sorbitan trioleate, sorbitan monostearate, sorbitan monopalmitate, sorbitan monolaurate, sucrose fatty acid ester, decaglyceryl monolaurate, decaglyceryl monostearate, decaglyceryl monooleate, and decaglyceryl monomyristate.

The cationic surfactant makes hair feel good in addition to the above-described actions. Examples of the cationic surfactant include quaternary ammonium salts. Examples of the quaternary ammonium salt include alkyltrimethylammonium chlorides, lauryltrimethylammonium chloride, cetyltrimethylammonium chloride, stearyltrimethylammonium chloride, stearyltrimethylammonium bromide, lauryltrimethylammonium bromide, and dialkyldimethylammonium chlorides.

Examples of the anionic surfactant include fatty acid salts, metallic soaps, acyl glutamates, acyl methyltaurates, alkylsulfates, alkyl ether sulfates, POE lauryl ether phosphoric acid or salts thereof, triethanolamine dodecylbenzenesulfonate, sodium tetradecenesulfonate, and sodium dioctyl sulfosuccinate. Examples of the fatty acid salt include coconut oil fatty acid potassium, coconut oil fatty acid triethanolamine, sodium laurate, potassium myristate, isopropanolamine myristate, sodium palmitate, sodium stearate, triethanolamine stearate, potassium oleate, and sodium oleate. Examples of the metallic soap include magnesium stearate, calcium stearate, and magnesium myristate. Examples of the acyl glutamate include potassium coconut oil fatty acid acyl glutamates, triethanolamine coconut oil fatty acid acyl glutamates, triethanolamine lauroyl glutamate, potassium myristoyl glutamate, and sodium stearoyl glutamate. Examples of the acyl methyltaurate include potassium lauroyl methyltaurate, sodium coconut oil fatty acid methyltaurate, sodium palmitoyl methyltaurate, and sodium stearoyl methyltaurate. Examples of the alkylsulfate include sodium laurylsulfate and triethanolamine laurylsulfate. Examples of the alkyl ether sulfate include sodium POE lauryl ether sulfate and triethanolamine POE lauryl ether sulfate.

Examples of the ampholytic surfactant include 2-alkyl-N-carboxymethyl-N-hydroxyethylimidazolinium betaines, lauryldimethylaminoacetic acid betaine, sodium undecylcarboxymethoxyethylcarboxymethylimidazolinium betaine, sodium undecylhydroxyethylimidazolinium betaine, undecyl-N-hydroxyethyl-N-carboxymethylimidazolinium betaine, alkyldiaminoethylglycine hydrochloride solutions, stearyldihydroxyethyl betaine, stearyldimethylaminoacetic acid betaine, sodium stearyldimethyl betaine solutions, bis(stearyl-N-hydroxyethylimidazoline)chloroacetic acid complex, sodium coconut oil alkyl-N-carboxyethyl-N-hydroxyethylimidazolinium betaines, disodium coconut oil alkyl-N-carboxyethoxyethyl-N-carboxyethylimidazolinium hydroxides, disodium coconut oil alkyl-N-carboxymethoxyethyl-N-carboxyethylimidazolinium hydroxides, disodium coconut oil alkyl-N-carboxymethoxyethyl-N-carboxyethylimidazolinium lauryl sulfates, coconut oil alkyl betaines, coconut oil fatty acid amidopropyl betaines, sodium coconut oil fatty acid-N-carboxymethoxyethyl-N-carboxyethylimidazolinium betaines, triethanolamine laurylaminopropionate, sodium β-laurylaminopropionate, disodium lauryl-N-carboxymethoxyethyl-N-carboxymethylimidazolinium dodecanoyl sarcosine, sodium lauryldiaminoethylglycine, lauric acid amidopropyl betaine solutions, lauryl sulfobetaine, and lauryl hydroxysulfobetaine.

The oily component facilitates the application of the oxidation hair dye composition to the hair and impart softness and moisture to the hair. Examples of the oily component include fat and oils, waxes, higher alcohols, hydrocarbons, higher fatty acids, alkyl glyceryl ethers, esters, and silicones.

Examples of the oil and fat include olive oil, camellia oil, shea butter, almond oil, tea fruit oil, sasanqua oil, safflower oil, sunflower oil, soybean oil, cottonseed oil, sesame oil, beef tallow, cacao butter, corn oil, peanut oil, rapeseed oil, rice bran oil, rice germ oil, wheat germ oil, pearl barley oil, grape seed oil, avocado oil, carrot oil, macadamia nut oil, castor oil, linseed oil, coconut oil, mink oil, and egg yolk oil. Examples of the wax include yellow beeswax, candelilla wax, carnauba wax, jojoba oil, and lanolin.

Examples of the higher alcohol include lauryl alcohol, myristyl alcohol, cetyl alcohol (cetanol), srearyl alcohol, cetostearyl alcohol, aralky alcohols, behenyl alcohol, 2-hexyldecanol, isostearyl alcohol, 2-octyldodecanol, decyltetradecanol, oleyl alcohol, linoleyl alcohol, linolenyl alcohol, and lanolin alcohol.

Examples of the hydrocarbon include α-olefin oligomers, light isoparaffin, light liquid isoparaffin, synthetic squalane, vegetal squalane, squalane, polybutene, liquid isoparaffin, liquid paraffin, ozokerite, ceresin, paraffin, powdered polyethylene, microcrystalline wax, and vaseline.

Examples of the higher fatty acid include lauric acid, myristic acid, palmitic acid, stearic acid, behenic acid, isostearic acid, hydroxystearic acid, 12-hydroxystearic acid, oleic acid, undecylenic acid, linoleic acid, ricinoleic acid, and lanolin fatty acid. Examples of the alkyl glyceryl ether include batyl alcohol (monostearyl glyceryl ether), chimyl alcohol (monocetyl glyceryl ether), selachyl alcohol (monooleyl glyceryl ether), and isostearyl glyceryl ether.

Examples of the ester include diisopropyl adipate, diisobutyl adipate, dioctyl adipate, 2-hexyldecyl adipate, diisostearyl adipate, isopropyl myristate, cetyl octanoate, cetyl isooctanoate, isononyl isononanoate, isodecyl isononanoate, isotridecyl isononanoate, diisopropyl sebacate, octyldodecyl myristate, isopropyl palmitate, butyl stearate, stearyl stearate, hexyl laurate, myristyl myristate, decyl oleate, hexyldecyl dimethyloctoate, triisodecyl myristate, isostearyl myristate, 2-ethylhexyl palmitate, octyldodecyl ricinoleate, fatty acid (C10-30) (cholesteryl/lanosteryl), lauryl lactate, cetyl lactate, myristyl lactate, octyldodecyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearates, cetyl caprate, glyceryl tricaprate, neopentylglycol dicaprate, diisostearyl malate, and lanolin derivatives.

Examples of the silicone include dimethyl polysiloxane, methylphenyl polysiloxane, decamethylcyclopentanesiloxane, dodecamethylcyclohexasiloxane, polyether-modified silicones, high-polymeric silicones having an average polymerization degree of 650 to 10,000, amino-modified silicones, betaine-modified silicones, alkyl-modified silicones, alkoxy-modified silicones, mercapto-modified silicones, carboxy-modified silicones, and fluorine-modified silicones. These oily components may be contained alone or in a combination of two kinds or more.

Examples of the polyvalent alcohol include glycols and glycerins. Examples of the glycols include ethylene glycol, diethylene glycol, triethylene glycol, propylene glycol, dipropylene glycol, isoprene glycol, and 1,3-butylene glycol. Examples of the glycerins include glycerin, diglycerin, and polyglycerin.

Examples of another component include saccharides such as sorbitol and maltose, water-soluble high molecular compounds such as gum arabic, karaya gum, gum tragacanth, sodium alginate, xanthan gum, cellulose derivatives, crosslinked polyacrylic acid, and polydimethylmethylenepiperidium chloride, preservatives such as paraben, chelating agents such as EDTA-2Na, stabilizers such as phenacetin, 8-hydroxyquinoline, acetanilide, sodium pyrophosphate, barbituric acid, uric acid, and tannic acid, pH adjustors such as phosphoric acid, citric acid, sulfuric acid, acetic acid, lactic acid, and tartaric acid, plant extracts, galenical extracts, vitamins, perfumes, and ultraviolet absorbers. In addition, the first agent may contain at least one selected from the components described in "Iyakubugaihin Genryo Kikaku (Japanese References of Quasi-drug Ingredients)" (issued by Yakuji Nippo Ltd. in June 1991).

The formulation of the first agent is not particularly restricted, and examples thereof include liquid, gel, foam, and cream forms. When the first agent has a liquid form, it is, for example, an aqueous solution, a dispersion, or an emulsion.

Second Agent

The second agent according to the present embodiment comprises an oxidizing agent. The oxidizing agent produces the oxidization polymerization of the oxidation dye and decolorizes the melanin contained in the hair. Examples of the oxidizing agent include hydrogen peroxide, urea peroxide, melamine peroxide, sodium percarbonate, potassium percarbonate, sodium perborate, potassium perborate, ammonium persulfate, sodium peroxide, potassium peroxide, magnesium peroxide, barium peroxide, calcium peroxide, strontium peroxide, hydrogen peroxide adducts of sulfates, hydrogen peroxide adducts of phosphates, and hydrogen peroxide adducts of pyrophosphates. These oxidizing agents may be contained alone or in a combination of two kinds or more. Among these oxidizing agents, preferred is hydrogen peroxide because it is excellent in melanin-decoloring power.

The content of the oxidizing agent in the oxidation hair dye composition is preferably 0.1 to 10.0 mass %, more preferably 0.5 to 8.0 mass %, most preferably 1.0 to 6.0 mass %. An oxidizing agent content of less than 0.1 mass % may be not capable of sufficiently decoloring the melanin. In addition, the oxidation dye can not sufficiently be color developed through oxidation. On the other hand, an oxidizing agent content of more than 10.0 mass % may induce troubles such as damage in the hair.

The second agent may contain the above-described other components for the first agent. When the second agent contains hydrogen peroxide as an oxidizing agent, it preferably contains a stabilizer to inhibit the decomposition of hydrogen peroxide. Examples of the stabilizer include urea, phenacetin, sodium stannate, ethylene glycol phenyl ether, 8-oxyquinoline, phosphoric acid, 1-hydroxyethane-1,1-diphosphonic acid and its salts, and dibutylhydroxytoluene. In addition, at least one of stabilizer selected from those described in "Iyakubugaihin Genryo Kikaku (Japanese References of Quasi-drug Ingredients)" (issued by Yakuji Nippo Ltd. in June 1991) may be contained.

The formulation of the second agent is not particularly restricted, and examples thereof include liquid, gel, foam, and cream forms. When the second agent has a liquid form, it is, for example, an aqueous solution, a dispersion, or an emulsion.

Oxidation Hair Dye Composition

In dyeing the hair, the above-described first and second agents are mixed in a prescribed ratio to provide the oxidation hair dye composition. The storage form and mixing method of the first and second agents are not particularly restricted. By way of example, the first and second agents may be charged in an aerosol container having a simultaneous spouting mechanism in which the first and second agents are charged in separate containers and are spouted in a mixed state from one outlet when spouted from the respective containers. A dedicated tray may be also used to mix and stir the first and second agents on the tray employing a brush. The formulation of the oxidation hair dye composition is not particularly restricted, and examples thereof include cream, gel, and foam forms.

According to the present embodiment described above, the following effects result.

(1) According to the embodiment, hyaluronic acids are contained in the oxidation hair dye composition to improve the dyeing property thereof.

(2) The hyaluronic acids suppress an increase in the viscosity of the oxidation hair dye composition because it achieves the effect of improving the hair-dyeing property in a small amount compared to, for example, a conventional animal-derived hyaluronic acid.

(3) According to the embodiment, sulfonic acids are contained in the oxidation hair dye composition. Thus, the dyeing property is improved by a synergistic effect between the hyaluronic acids and the sulfonic acids.

(4) When the hyaluronic acids are extracted and purified from the fermentation culture medium of the genus *Streptococcus*, the hyaluronic acids is produced or acquired at low cost.

The above-described embodiment may be also modified as follows.

According to the above-described embodiment, the hyaluronic acids and the sulfonic acids are contained in the first agent. However, the hyaluronic acids and the sulfonic acids may be contained in both of the first and second agents, or may be contained only in the second agent.

According to the above-described embodiment, the oxidation hair dye composition is composed of the first and second agents, which are mixed immediately before the use of the oxidation hair dye composition. However, the oxidation hair dye composition may also be composed of a three-or-more-agent type by separating the components constituting the first and second agents. By way of example, the oxidation hair dye composition may be composed of a first agent comprising the oxidation dye and hyaluronic acids, a second agent comprising the alkaline chemical, and a third agent comprising the oxidizing agent.

EXAMPLE

The above-described embodiment will now be more specifically described with reference to Examples and Comparative Examples.

Examples 1 to 11 and Comparative Examples 1 to 3

The components shown in Table 1 or 2 were mixed to prepare first and second agents according to each Example or Comparative Example. Then, the first and second agents according to each Example or Comparative Example were mixed in a mass ratio of 1:1 to prepare a hair dye composition. The prepared hair dye composition was applied to a human white hair bundle (hereinafter simply referred to as "hair bundle") using a brush, followed by allowing to stand at 25° C. for 30 minutes. Subsequently, the hair dye composition adhering to the hair bundle was flushed with water, followed by applying, to the hair bundle, a shampoo twice and further a rinse once. Water was then wiped off from the hair bundle using a towel, followed by drying the bundle employing a drier to provide a dye-treated hair bundle. This dye-treated hair bundle was used to evaluate the hair-dyeing property of the hair dye composition. The evaluation results are shown in Tables 1 and 2. In Tables 1 and 2, the unit of numerical values in a column indicating each component is mass %. 1% Sodium Biohyaluronic Acid Solution from Shiseido Co., Ltd. (a mixture of 1% of microbial (*Streptococcus*) sodium hyaluronate, 0.10% of methylparaben, 0.12% of phenoxyethanol, and 98.78% of ion-exchanged water (MP-PE)) was used as a microbial sodium hyaluronate. In the tables, the numeral values in the column of "microbial sodium hyaluronate" indicate the final concentrations of the microbial sodium hyaluronate per se in the hair dye compositions.

Evaluation of Hair-Dyeing Properties

The dye-treated hair bundle of Comparative Example 2 which was treated with a hair dye composition containing no hyaluronic acid was used as a standard hair bundle. In the "hair-dyeing property" column of each Table, "4" indicates that the dye-treated hair bundle was considerably more deeply dyed than the standard hair bundle, and "3" indicates that the dye-treated hair bundle was evidently more deeply dyed than the standard hair bundle. "2" indicates that the dye-treated hair bundle was more deeply dyed than the standard hair bundle; "1" indicates that the dye-treated hair bundle was slightly more deeply dyed than the standard hair bundle; and "0" indicates that the dyeing degree of the dye-treated hair bundle was not different from that of the standard hair bundle. These evaluations were carried out by an expert panelist visually observing each dye-treated hair bundle.

TABLE 1

|  | Examples | | | | | |
|---|---|---|---|---|---|---|
|  | 1 | 2 | 3 | 4 | 5 | 6 |
| First agent | | | | | | |
| Microbial sodium hyaluronate | 0.01 | 0.005 | 0.005 | 0.005 | 0.005 | 0.005 |
| Cockscomb-derived sodium hyaluronate | — | — | — | — | — | — |
| Taurine | — | 0.005 | — | — | — | — |
| Dihydroxydimethoxybenzophenonedisulfonic acid | — | — | 0.005 | — | — | — |
| Para-phenolsulfonic acid | — | — | — | 0.005 | — | — |
| Pantetheine-S-sulfonic acid | — | — | — | — | 0.005 | — |
| Hydroxymethoxybenzophenonesulfonic acid | — | — | — | — | — | 0.005 |
| Guaiazulenesulfonic acid | — | — | — | — | — | — |
| Cetostearyl alcohol | 3.0 | 3.0 | 3.0 | 3.0 | 3.0 | 3.0 |
| Propylene glycol | 5.0 | 5.0 | 5.0 | 5.0 | 5.0 | 5.0 |
| POE cetyl ether | 4.0 | 4.0 | 4.0 | 4.0 | 4.0 | 4.0 |
| Sodium lauryl sulfate | 1.0 | 1.0 | 1.0 | 1.0 | 1.0 | 1.0 |
| Anhydrous sodium sulfite | 0.1 | 0.1 | 0.1 | 0.1 | 0.1 | 0.1 |
| Strong ammonia water (28%) | 5.0 | 5.0 | 5.0 | 5.0 | 5.0 | 5.0 |
| Para-phenylenediamine | 1.0 | 1.0 | 1.0 | 1.0 | 1.0 | 1.0 |
| Purified water | Remaining quantity | Remaining quantity | Remaining quantity | Remaining quantity | Remaining quantity | Remaining quantity |
| Second agent | | | | | | |
| 35% hydrogen peroxide solution | 15.0 | 15.0 | 15.0 | 15.0 | 15.0 | 15.0 |
| Cetanol | 3.0 | 3.0 | 3.0 | 3.0 | 3.0 | 3.0 |
| Sodium lauryl sulfate | 0.5 | 0.5 | 0.5 | 0.5 | 0.5 | 0.5 |
| Purified water | Remaining quantity | Remaining quantity | Remaining quantity | Remaining quantity | Remaining quantity | Remaining quantity |

TABLE 1-continued

| Hair-dyeing property | 3 | 4 | 4 | 4 | 4 | 4 |
| --- | --- | --- | --- | --- | --- | --- |
| | | Examples | | | | |
| | | 7 | 8 | 9 | 10 | 11 |
| First agent | | | | | | |
| Microbial sodium hyaluronate | | 0.005 | 0.00005 | 0.0001 | 0.0005 | 0.5 |
| Cockscomb-derived sodium hyaluronate | | — | — | — | — | — |
| Taurine | | — | 0.005 | 0.005 | 0.005 | 0.005 |
| Dihydroxydimethoxybenzo-phenonedisulfonic acid | | — | — | — | — | — |
| Para-phenolsulfonic acid | | — | — | — | — | — |
| Pantetheine-S-sulfonic acid | | — | — | — | — | — |
| Hydroxymethoxybenzophenonesulfonic acid | | — | — | — | — | — |
| Guaiazulenesulfonic acid | | 0.005 | — | — | — | — |
| Cetostearyl alcohol | | 3.0 | 3.0 | 3.0 | 3.0 | 3.0 |
| Propylene glycol | | 5.0 | 5.0 | 5.0 | 5.0 | 5.0 |
| POE cetyl ether | | 4.0 | 4.0 | 4.0 | 4.0 | 4.0 |
| Sodium lauryl sulfate | | 1.0 | 1.0 | 1.0 | 1.0 | 1.0 |
| Anhydrous sodium sulfite | | 0.1 | 0.1 | 0.1 | 0.1 | 0.1 |
| Strong ammonia water (28%) | | 5.0 | 5.0 | 5.0 | 5.0 | 5.0 |
| Para-phenylenediamine | | 1.0 | 1.0 | 1.0 | 1.0 | 1.0 |
| Purified water | | Remaining quantity | Remaining quantity | Remaining quantity | Remaining quantity | Remaining quantity |
| Second agent | | | | | | |
| 35% hydrogen peroxide solution | | 15.0 | 15.0 | 15.0 | 15.0 | 15.0 |
| Cetanol | | 3.0 | 3.0 | 3.0 | 3.0 | 3.0 |
| Sodium lauryl sulfate | | 0.5 | 0.5 | 0.5 | 0.5 | 0.5 |
| Purified water | | Remaining quantity | Remaining quantity | Remaining quantity | Remaining quantity | Remaining quantity |
| Hair-dyeing property | | 4 | 3 | 3 | 4 | 3 |

TABLE 2

| | Comparative Examples | | |
| --- | --- | --- | --- |
| | 1 | 2 | 3 |
| First agent | | | |
| Microbial sodium hyaluronate | — | — | — |
| Cockscomb-derived sodium hyaluronate | 0.01 | — | — |
| Taurine | — | — | 0.01 |
| Dihydroxydimethoxybenzo-phenonedisulfonic acid | — | — | — |
| Para-phenolsulfonic acid | — | — | — |
| Pantetheine-S-sulfonic acid | — | — | — |
| Hydroxymethoxybenzophenone-sulfonic acid | — | — | — |
| Guaiazulenesulfonic acid | — | — | — |
| Cetostearyl alcohol | 3.0 | 3.0 | 3.0 |
| Propylene glycol | 5.0 | 5.0 | 5.0 |
| POE cetyl ether | 4.0 | 4.0 | 4.0 |
| Sodium lauryl sulfate | 1.0 | 1.0 | 1.0 |
| Anhydrous sodium sulfite | 0.1 | 0.1 | 0.1 |
| Strong ammonia water (28%) | 5.0 | 5.0 | 5.0 |
| Para-phenylenediamine | 1.0 | 1.0 | 1.0 |
| Purified water | Remaining quantity | Remaining quantity | Remaining quantity |
| Second agent | | | |
| 35% hydrogen peroxide solution | 15.0 | 15.0 | 15.0 |
| Cetanol | 3.0 | 3.0 | 3.0 |
| Sodium lauryl sulfate | 0.5 | 0.5 | 0.5 |
| Purified water | Remaining quantity | Remaining quantity | Remaining quantity |
| Hair-dyeing property | 0 | — | 1 |

The results in Tables 1 and 2 demonstrated that the hair-dyeing properties were improved in all of Examples 1 to 11 compared to that of the standard hair bundle. Particularly in Examples 2 to 7, it was demonstrated that the hair-dyeing properties were drastically improved compared to that of the standard hair bundle when the microbial sodium hyaluronate and a compound having a particular sulfonic acid group were used in combination. It was estimated and recognized particularly from Examples 8 to 11 that the content of each of the hyaluronic acids was set to within the range of 0.00001 to 0.3 mass % to improve the hair-dyeing property compared to that of the standard hair-bundle. On the other hand, it was demonstrated that the effect of sufficiently improving the hair-dyeing property was not achieved when the sodium hyaluronate, other than the microbial sodium hyaluronate, was used or when each of the sulfonic acids was used alone.

The invention claimed is:

1. An oxidation hair dye composition comprising:
   an oxidation dye,
   an alkaline chemical,
   an oxidizing agent, and
   at least one component selected from the group consisting of microbial hyaluronic acids and salts thereof.

2. The oxidation hair dye composition according to claim 1, wherein the content of at least component one selected from the group consisting of said microbial hyaluronic acids and salts thereof in the composition is 0.00001 to 0.3 mass %.

3. The oxidation hair dye composition according to claim 1, further comprising at least one component selected from the group consisting of hydroxymethoxybenzophenone-sulfonic acid, dihydroxydimethoxybenzophenonedisulfonic acid, pantetheine-S-sulfonic acid, aminoethylsulfonic acid, guaiazulenesulfonic acid, para-phenolsulfonic acid, and salts thereof.

4. The oxidation hair dye composition according to claim 3, wherein the ratio of the content of at least one component selected from the group consisting of microbial hyaluronic acids and salts thereof to the content of at least one selected from the group consisting of said hydroxymethoxybenzophenonesulfonic acid, dihydroxydimethoxybenzophenonedisulfonic acid, pantetheine-S-sulfonic acid, aminoethylsulfonic acid, guaiazulenesulfonic acid, paraphenolsulfonic acid, and salts thereof is 1:100 to 100:1.

5. The oxidation hair dye composition according to claim 3, wherein the content of at least one component selected from the group consisting of said hydroxymethoxybenzophenonesulfonic acid, dihydroxydimethoxybenzophenonedisulfonic acid, pantetheine-S-sulfonic acid, aminoethylsulfonic acid, guaiazulenesulfonic acid, paraphenolsulfonic acid, and salts in the composition is 0.000001 to 5 mass %.

* * * * *

UNITED STATES PATENT AND TRADEMARK OFFICE
CERTIFICATE OF CORRECTION

PATENT NO.        : 7,658,769 B2
APPLICATION NO.   : 11/914687
DATED             : February 9, 2010
INVENTOR(S)       : Tsuyoshi Nonogaki It is certified that error appears in the above-identified patent and that said Letters Patent is hereby corrected as shown below:

Column 1
Lines 12-15 Delete "This oxidation hair dye composition of a liquid formulation thereof for improving the permeability typically also contains an alkaline chemical to elevate the pH of oxidatino dye." and insert therefor -- This oxidation hair dye composition typically also contains an alkaline chemical to elevate the pH of a liquid formulation thereof for improving the permeability of the oxidation dye. --

Signed and Sealed this

Twenty-seventh Day of April, 2010

David J. Kappos
Director of the United States Patent and Trademark Office